United States Patent [19]

Jessup et al.

[11] 4,400,284

[45] Aug. 23, 1983

[54] BORON DERIVATIVES AS LUBRICANT ADDITIVES

[75] Inventors: Peter Jessup, Santa Ana; Richard A. Holstedt, Whittier; Kenneth Baron, Diamond Bar, all of Calif.

[73] Assignee: Union Oil Company of California, Los Angeles, Calif.

[21] Appl. No.: 158,828

[22] Filed: Jun. 12, 1980

[51] Int. Cl.³ ........................... C10M 3/48; C07F 5/04
[52] U.S. Cl. ................................. 252/49.6; 260/462 R
[58] Field of Search .................... 252/49.6; 260/462 R

[56] References Cited

U.S. PATENT DOCUMENTS

| | | | |
|---|---|---|---|
| 2,234,581 | 3/1911 | Rosen | 252/49.6 |
| 2,441,063 | 5/1948 | Gilman | 260/462 R |
| 2,987,476 | 6/1961 | Hartley et al. | 252/49.6 |
| 3,185,644 | 5/1965 | Knowles et al. | 252/49.6 |
| 3,224,991 | 12/1965 | Knowles et al. | 260/462 R |
| 3,227,739 | 1/1966 | Versteeg | 260/462 |
| 3,232,876 | 2/1966 | Abend | 252/49.6 |
| 3,269,853 | 8/1966 | English | 260/462 R |
| 3,313,727 | 4/1967 | Peeler | 252/49.6 |
| 3,321,506 | 5/1967 | Knowles et al. | 252/49.6 |
| 3,338,834 | 8/1967 | Abbott | 252/49.6 |
| 3,429,909 | 2/1969 | Schuster | 260/462 R |
| 3,598,757 | 8/1971 | Cyba | 252/400 |
| 3,598,855 | 8/1971 | Cyba | 252/49.6 |
| 3,642,652 | 2/1972 | Birgy | 260/462 R |
| 3,764,593 | 10/1973 | Schuster | 260/462 R |
| 3,912,643 | 10/1975 | Adams | 252/49.6 |
| 3,912,644 | 10/1975 | Adams | 252/49.6 |
| 4,136,039 | 1/1979 | Jäger | 260/462 R |
| 4,176,076 | 11/1979 | Waldstein | 252/49.6 |
| 4,204,972 | 5/1980 | Knoblauch et al. | 260/462 R |

OTHER PUBLICATIONS

Morrison and Boyd, *Organic Chemistry*, 1966, p. 66.
*Condensed Chemical Dictionary*, 7th edition, Reinhold Pub. Comp., pp. 31-32.
Weast, *Handbook of Chemistry and Physics*, 61st edition, section C-1, paragraph 1.2.

*Primary Examiner*—Delbert E. Gantz
*Assistant Examiner*—Raymond Covington
*Attorney, Agent, or Firm*—Dean Sandford; Gregory F. Wirzbicki; Cleveland R. Williams

[57] ABSTRACT

Boron and/or metal-boron derivatives having extreme pressure anti-wear and friction reducing properties and lubricating compositions containing the same are disclosed. The lubricating compositions comprise a major amount of a lubricating oil and a minor amount of an extreme pressure, anti-wear and friction reducing additive comprising a boramid or metal containing boramid compound.

16 Claims, No Drawings

BORON DERIVATIVES AS LUBRICANT ADDITIVES

FIELD OF THE INVENTION

This invention relates to lubricating oils, and more particularly to anti-wear, friction reducing and extreme pressure lubricating oils and additives therefor. Anti-wear, friction reducing and extreme pressure (or "E.P.") additives, as they are commonly called, are chemicals which are added to lubricating compositions to reduce friction and reduce or prevent destructive metal-to-metal contact in the lubrication of moving surfaces. Lubricating oils provide good lubrication between moving surfaces in contact with each other, as long as a film of said oil is maintained between the relatively moving surfaces. This particular kind of lubrication is commonly termed "hydrodynamic lubrication". However, when pressure and/or rubbing speeds between moving metal surfaces are such that the film of lubricating oil is no longer intact, metal-to-metal contact and wear occur over a significant portion of the previously lubricated area. Under such conditions, a kind of lubrication called boundary lubrication is needed, and is governed by parameters of the contacting surfaces, such as, surface finish, hardness, metal shear strength, and the coefficient of friction between the metals involved. Destructive metal-to-metal contact, due to lack of lubrication under extreme conditions, manifests itself in different forms such as scoring, welding, scuffing, ridging, rippling, rapid wear, and in some cases deformation or complete destruction of the metal components.

Extreme pressure, anti-wear and friction reducing lubricating additives prevent destructive metal-to-metal contact, under boundary lubrication conditions, by adsorption or reacting with relatively moving metal surfaces to form an adherent, protective film of compounds which have a lower shear strength than that of the metal surfaces. This film acts in the capacity of a "boundary lubricant" and performs the function of lubrication when metal-to-metal contact occurs. Boundary conditions and boundary lubricant refer to the conditions and a suitable lubricant relating to the combination of applied load, fluid viscosity and rubbing speed, which do not allow hydrodynamic lubrication to exist. Hydrodynamic lubrication exists when a film of lubricant maintains separation between lubricated surfaces.

Many extreme pressure and anti-wear agents are oil soluble or easily dispersed as a stable dispersion in oil. Many of the E.P. agents which provide the high load capacity are chemically reactive, containing chlorine, sulfur or phosphorus which react with metal surfaces.

It has now been discovered that certain oil-soluble or dispersible boron or metal-boran derivatives prepared as described herein, when added to lubricating oils or grease not only improve the ability of the lubricant to prevent seizure of the parts being lubricated but in addition greatly reduce the amount of friction and wear of such moving parts. We have synthesized a new family of extreme pressure and anti-wear compounds which are boron derivatives and/or reaction products of "boramids", and metal salts thereof, as described further herein.

DESCRIPTION OF THE PRIOR ART

The use of boron containing compounds as extreme pressure and anti-wear additives for lubricating oils is known and appreciated by the prior art. For example, U.S. Pat. No. 3,313,727 to Peeler discloses compositions of amorphous alkali metal borates as a stable dispersion in lubrication oils. In particular, a boron compound, such as, the metaborates and tetraborates of sodium and potassium in combination with a lyophilic surface active agent, such as, the carboxylates, phenates and sulfonates of alkaline earth metals, e.g. calcium and barium, when dispersed in lubricating oil compositions are said to improve the extreme pressure and anti-wear properties thereof.

U.S. Pat. No. 2,987,476 to Hartley et al. relates to a method for solubilizing boric acid and metal borates in liquid fuels for internal combustion engines and in lubricating oils and greases. Desirable compositions are prepared by hydrolyzing an organic ester of boric acid in the presence of three materials, namely, a lyophilic ionic surface active agent, a non-polar organic liquid and a water-miscible organic liquid. The resulting dispersible boron-containing product of this process is a complex of an inorganic boric acid compound with an oleophilic ionic surface active agent.

Another boron composition is disclosed in U.S. Pat. No. 3,598,855 to Cyba which relates to cyclic borates of polymeric alkanolamines formed by reacting a borylating agent with a polymeric alkanolamine. The additives thus formed are described as additives for a wide variety of petroleum products including lubricating oils.

U.S. Pat. No. 3,227,739 to Versteeg relates to lubricating oils containing additives formed by reacting certain amine type compounds with boric acid. The amine type compounds are prepared by reacting equal molar proportions of diethanolamine or dipropanolamine and a long chain 1,2-epoxide.

Another extreme pressure lubrication composition is disclosed in U.S. Pat. No. 3,185,644 to Knowles et al., which relates to lubricating compositions containing amine salts of boron-containing compounds. The amine salts are formed by reaction of a hydroxy substituted amine and a trihydrocarbyl borate. The amine-borate compounds thus formed are described as useful as load carrying additives for mineral and synthetic base lubricating oils.

From the foregoing, it can readily be seen that there is an ongoing search for extreme pressure, anti-wear and friction reducing lubricating compositions which contain boron and/or metal-boron derivatives.

SUMMARY OF THE INVENTION

This invention resides in an extreme pressure, anti-wear, and friction reducing lubrication composition comprising a major amount of a lubricating oil and a minor amount of an extreme pressure, anti-wear additive of the formula:

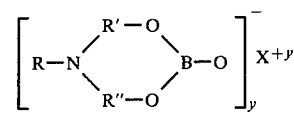

wherein R is hydrogen, alkyl, cyclic, alicyclic, aryl, alkylaryl, or arylalkyl radicals having from 1 to about 24 carbon atoms, R' and R" are straight or branched carbon chains, cyclic, alicyclic, aryl, alkylaryl or arylalkyl radicals having from 2 to about 20 carbon atoms, Y is an integer of 1 to 4, and X is either hydrogen, a transition metal having an atomic number between 21 and 30 or a Group IVA metal of the Periodic Table and mixtures thereof.

DESCRIPTION OF THE INVENTION

The present invention resides in extreme pressure, anti-wear and friction reducing lubricating oil compositions comprising a major amount of an oil of lubrication viscosity and as an extreme pressure and anti-wear additive a minor amount of a boron or metal-boron derivative as described hereinbelow.

The terms "friction reducing and anti-wear" herein refer to the ability of a substance to reduce the coefficient of friction between sliding or rubbing surfaces and/or the ability of a substance to prevent metal-to-metal welding or bonding during rubbing at extremely high contact pressures. "Extreme pressure lubricant" refers to a fluid or other substance which provides lubrication during extreme pressure conditions, including boundary lubrication. The term boramid denotes the reaction product of a primary amine, an alkylene oxide or epoxide and boric acid, all of which are further described herein. Metal derivatives of boramids are the reaction product of the desired metal and specified boramid compound.

The extreme pressure and anti-wear additives described herein may be incorporated in a wide variety of lubricating oils, for example, mineral oil, (including automobile engine oil), crude oil, synthetic oil, industrial oils, for example, cutting oil, metal working fluids and grease. For example, the additives may be added to lubricating oils derived from paraffins, naphthenic or mixed base crude petroleum oils, that have been subjected to solvent and/or sulfuric-acid treatment, aluminum chloride treatment, hydrogenation and/or other refining treatments. In addition, the additives described herein may be incorporated in petroleum distillates, such as diesel fuel, jet engine fuel, furnace oil, gas oil and other light oils. The petroleum oils may be virgin or cracked petroleum stock, or mixtures thereof, boiling in the range of about 100° F. to about 1,100° F. The petroleum oil may contain cracked components such as those derived from cycle oils or cycle cuts boiling above gasoline, usually in the range of about 450° F. to about 750° F. and may be derived by catalytic or thermal cracking. Oils of high or low sulfur content such as diesel fuels or oils may additionally be used.

Preferred distillate lubrication oils which are improved by the addition of additives herein have an initial boiling point within the range of 350° F. to about 475° F., an end point in the range of about 500° F. to about 1,100° F., and a flash point not lower than 110° F.

Lubricants derived from oil shale are particularly desirable for use herein. Oil shale is broadly defined as a variety of compact sedimentary rock, generally laminated, that contains little or no oil but does contain organic material, derived from aquatic organisms or waxy spores and pollen grains, which is convertible to oil by heat. Crude shale oil, in combination with water, gas and spent shale containing a carbonaceous residue and mineral matter, is formed by the pyrolysis of oil shale. The hydrocarbons of shale oil are highly unsaturated, resembling the products of thermal cracking of petroleum, as would be expected because of the pyrolytic origin of shale oil. Once the shale oil is extracted, it is subjected to conventional hydrotreating procedures to produce a variety of hydrocarbon products, including lubricants.

Synthetic lubricating oils as defined herein are those oils derived from a product of chemical synthesis (manmade oils). Typical examples of such compositions include the polyglycol fluids (i.e., polyalkaylene glycol); silicones which consist of a silicone-oxygen polymer chain to which are attached hydrocarbon branches composed of either alkyl or phenyl groups; phosphates; polyphenyl esters; synthetic hydrocarbons and various esters of organic acids and alcohols.

The polyalkylene glycol lubricating oils suitable for use herein preferably are derived from the reaction product of the appropriate alkylene oxides. The alkylene moiety of the above compositions have a carbon chain of from about 1 to about 10 carbon atoms, preferably from about 2 to about 7 carbon atoms and a molecular weight within the range of from about 200 to about 2,000, especially from about 200 to about 1,000, most preferably from about 200 to about 800. Representative examples of suitable polyalkylene glycols include, polyethylene glycol, polypropylene glycol, polyisopropylene glycol, polybutylene glycol and the like.

Silicone lubricants have extra-ordinary low viscosity-temperature coefficients coupled with good oxidation stability. The lubricant contains a repeating silicon-oxygen backbone and has organic groups R, wherein R is methyl, phenyl, vinyl and the like. The silicones herein have an average molecular weight within the range of from about 400 to about 9,000.

The polyphenyl ethers suitable for use herein have from 3 to 7 benzene rings and from 1 to 6 oxygen atoms, with the stated oxygen atoms joining the stated benzene rings in chains as ether linkages. One or more of the stated benzene rings in these polyphenyl ethers may be hydrocarbonyl-substituted. The hydrocarbonyl substituents, for thermal stability, must be free of CH and aliphatic CH so that preferred aliphatic substituents are lower saturated hydrocarbon radicals (1 to 6 carbon atoms) like methyl and tert-butyl, and preferred aromatic substituents are aryl radicals like phenyl and tolyl. In the latter case, the benzene ring supplied in the hydrocarbonyl substituent contributes to the total number of benzene rings in the molecule. Polyphenyl ethers consisting exclusively of chains of from 3 to 7 benzene rings with at least one oxygen atom joining the stated benzene rings in the chains as an ether linkage have particularly desirable thermal stability.

Exemplary of the alkyl polyphenyl ethers suitable for use are 3-ring polyphenyl ethers like 1-(p-methylphenoxy)4-phenoxybenzene and 2,4-diphenoxy-1-methyl-benzene, 4-ring polyethers like bis [p-(p-methylphenoxy)phenyl] ether and bis [(p-tert-butlphenoxy)-phenyl] ether, and the like.

Polyphenyl ethers consisting exclusively of benzene rings and ether oxygen atoms linking said rings are exemplified by the triphenoxy benzenes and aryl-substituted polyphenyl ethers such as biphenyl phenoxyphenyl ether, biphenylyloxyphenyl phenoxyphenyl ether, biphenylyl ether, dibiphenylyloxybenzene, bis(phenylyloxyphenyl) ether, and the like.

A preferred class of polyphenyl ethers comprises those consisting of benzene rings joined in a chain by oxygen atoms as ether linkages between each ring. Examples of the polyphenyl ethers contemplated in the class are the bis(phenoxy-phenyl)ethers (4 benzene rings joined in a chain by 3 oxygen atoms), illustrative of which is bis(m-phenoxy-phenyl) ether. The bis(-phenoxy-phenoxy) benzenes are particularly preferred in the present invention. Illustrative of these are m-bis(m-phenoxy-phenoxy) benzene, m-bis(p-phenoxy-phenoxy) benzene, o-bis(o-phenoxy-phenoxy) benzene, and so forth. Further, the polyphenyl ethers suitable for use herein include the bis(phenoxy-phenoxy-phenyl) ethers such as bis[m-(m-phenoxy-phenoxy) phenyl] ether, bis[p-(p-phenoxy-phenoxy phenyl] ether, m-(m-phenoxy-phenoxy)phenyl m-(o-phenoxy-phenoxy) phenyl ether and the bis (phenoxy-phenoxy-phenoxy) benzenes such as m-bis[m-phenoxy-phenoxy-phenoxy] benzene, p-bis[p-(m-phenoxy-phenoxy)phenoxy] benzene and m-bis[m-phenoxy-phenoxy)phenoxy] benzene.

Synthetic lubricating oils derived from hydrocarbons are generally of two types, namely, dialkylated benzene and polymerized alpha-olefins. Dialkylated benzene herein is formed from the condensation product of the appropriate alkyl compound and has a carbon chain from about 5 to about 50 carbon atoms, preferably from about 8 to about 20 carbon atoms; and a molecular weight of from about 200 to about 1,500, preferably from about 300 to about 700. Representative compounds include di-n-decylbenzene, n-decyl-n-tetradecylbenzene, and n-nonyl-n-dodecylbenzene.

Alpha-olefins suitable for use in preparing lubricating oils herein are characterized by the formula $RCH=CH_2$, wherein R is a radical selected from the group of hydrogen and alkyl radicals having from about 4 to about 18 carbon atoms, preferably from about 6 to about 10 carbon atoms, and having a molecular weight of from about 80 to about 300, preferably from about 100 to about 200. Typical compounds include 1-octene, 1-decene and 1-dodecene.

Phosphates suitable for use herein as synthetic lubricating oils are the phosphate esters having the formula $O=P(OR)_3$, wherein R is aryl or alkyl having from aobut 4 to about 20 carbon atoms, preferably from 6 to about 10 carbon atoms, and have a molecular weight within the range of from about 200 to about 1,000, preferably from about 300 to about 550. Representative compounds include trioctyl phosphate, tricresyl phosphate and dicresyl methyl phosphate.

Esters of organic acids which are suitable for use herein as synthetic lubricating oils preferably are selected from organic acids having carbon chains of from $C_4$ to $C_{40}$ carbon units. Organic acids which may be reacted with the alcohols herein include caproic, decanoic, sebacic, laurel, oleic, stearic, palmitic etc. Likewise, alcohols herein may be derived from either natural or synthetic origin for example, pentaerythritol, trimethylolpropane, amyl, 2-ethylhexanol or laurel alcohol, may be used to form the desired ester. The esters are formed using conventional methods. For example, the esters may be prepared by reaction of the desired alcohol with the desired acid, acid anhydride or acid halide using conventional reaction conditions and techniques.

Synthetic lubricating oils which are improved by the addition of the additives herein additionally include those derived from solid carbonaceous products, conveniently prepared by blending finely ground carbonaceous materials with a solvent to form a slurry. The slurry is then introduced into a reaction vessel containing a conventional hydrogenation catalyst and is reacted under normal hydrogenating pressures and temperatures. After hydrogenation, solids that are present may conveniently be removed from the product stream. The product is next stripped of solvent. The balance of the product stream may be distilled to obtain products of various boiling ranges, for example, hydrocarbons boiling in the gasoline range and hydrocarbons boiling in the lubricating oil range. Some of the products are useful as fuels and oils, the remainder may be further treated by a conventional petroleum process including cracking, hydrocracking, and the like. Synthetic lubricating oils produced from solid carbonaceous products, such as coal, are primarily aromatic and generally have a boiling range of about 300° F. to about 1,400° F., a density of about 0.1 to about 1.1 and a carbon to hydrogen molecular ratio in the range of about 1.3:1 to about 0.66:1. A typical example is a lubricating oil obtained from a subbituminous coal, such as Wyoming-Montana coal, comprising a middle oil having a boiling range of from about 375° F. to about 675° F. A description of how to prepare synthetic lubricating oils from a carbonaceous material, for example coal, is set forth in greater detail in U.S. Pat. No. 3,957,619 issued to Chun et al. on May 18, 1976, the disclosure of which is incorporated herein by reference.

Alternatively, the synthetic oil improved herein may be a nonhydrocarbon oil of lubricating viscosity. Suitable examples include synthetic oils obtained by polymerization of lower molecular weight alkylene oxides, such as propylene oxide and/or ethylene oxide employing alcohol or acid initiators, such as lauryl alcohol or acetic acid. Other typical synthetic oils include esters, for example, di(2-ethylhexyl)-silicate, tricresylphosphate and silicate esters, such as tetra-(2-ethyl-hexyl)-orthosilicate and hexa-(2-ethylbutoxy)-disiloxane.

If desired, the extreme pressure, anti-wear and friction reducing additives described herein may be employed in conjunction with other additives commonly used in petroleum products. Thus, there may be added to the oil compositions of this invention rust and corrosion inhibitors, emuslifying agents, antioxidants, dyes, haze inhibitors, anti-static agents, detergents, dispersants, viscosity index improvement agents and pour point reducing agents. Soaps or other thickening agents may be added to the lubricating oil compositions to form compositions having the consistency of a grease. When other additives are employed, it may be desirable, although not necessary to prepare additive concentrates comprising concentrated solutions of the herein boron or metal-boron derivatives together with said other additives whereby the several additives are added simultaneously. Dissolution of the additive or additive concentrate into the oil composition may be facilitated by mixing accompanied with mild heating, but this is not absolutely essential.

Metal-working fluids such as cutting and grinding fluids are defined as liquids applied to a cutting tool or apparatus to assist in a cutting or machining process by washing away chips or serving as a lubricant or coolant, for example, in milling, drilling, turning, cutting, threading, broaching, surface grinding, form grinding, flute grinding, and similar metal-working operations. These oils are preferably obtained from conventionally refined lubricating oils containing film-strength additives, or sulfurized naphthene-base oils which may additionally contain emulsifying agents. Representative fluids and agents include: water, water solutions or emulsions of detergents and oils, mineral oils, fatty oils, chlorinated mineral oils, sulfurized mineral oils and mixtures thereof.

The herein described extreme pressure, anti-wear and friction reducing additives may be incorporated in the lubricating oils in any convenient way. Thus, the boron or metal-boron derivatives may be added directly to the oil by dissolving the desired boron derivatives in the lubricating oil at the desired level of concentration.

Normally, the additive comprising boron or metal-boron derivatives is blended with the lubricating oil from about 0.1 to about 15 percent by weight, preferably from about 0.5 to about 10 percent by weight of the oil composition. Alternatively, the additive may be blended with suitable solvents to form concentrates that may readily be dissolved in the appropriate oil at the desired concentration. If a concentrate is employed, it ordinarily will contain at least 10 to about 65 percent by weight of the additive and preferably from 25 to about 65 percent by weight of said additive. The solvent in such a concentrate may be present in amounts of about 35 to about 75 percent by weight. Suitable solvents which may be used for this purpose are naphtha, and light mineral oil (i.e., 150 neutral to 450 neutral) and mixtures thereof. The particular solvent selected should, of course, be selected so as not to adversely affect the other desired properties of the ultimate oil composition. Thus, the solvent for use in incorporating the additive in a fuel oil should be compatible with the fuel in terms of stability, boiling range, corrosiveness, etc.

The extreme pressure, anti-wear additives of the present invention are represented by the following formula:

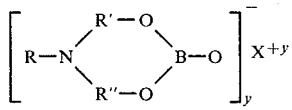

wherein R is hydrogen, alkyl, cyclic, alicyclic, aryl, alkylaryl, or arylalkyl radicals having from 1 to about 24 carbon atoms, preferably from 1 to about 18 carbon atoms, R' and R" are straight or branched carbon chains, cyclic, alicyclic, aryl, alkyaryl, or arylalkyl radicals having from 2 to about 20 carbon atoms, especially from about 2 to about 10 carbon atoms, y is an integer from 1 to 4, and X is either hydrogen or a metal selected from transition metals having an atomic number between 21 and 30 or a Group IVA metal of the Periodic Table and mixtures thereof.

The above group of compounds, including metal derivatives thereof are referred to as boramids. The above compounds are conveniently prepared by reacting a primary amine with an alkylene oxide or epoxide. The resulting product is, then reacted with boric acid to give the corresponding boramid compound. Amines which are suitable for use herein include methylamine, ethylamine, propylamine, butylamine, octadecylamine, dodecylamine, cyclohexylamine, phenylamine, cocoamine, tallowamine and oleylamine and mixtures thereof. A wide variety of alkene oxides or epoxides may be used to prepare the precursor for the boramid compounds herein. Typical alkene oxides or epoxides which are suitable for use include ethylene oxide, propylene oxide, 1,2-epoxybutane, cyclohexane oxide, cyclooctene oxide, cyclododecene oxide, and 1,2-epoxybenzene and mixtures thereof. Normally, the boron atom will comprise from about 0.5 to about 10 weight percent, especially from about 2 to about 5 weight percent of the boramid compound. The boramid and/or metal-boramid compounds produced in accordance with the procedure herein are preferably selected from the group comprising methylaminodiethylate hydrogen borate, ethylaminodiethylate hydrogen borate, propylaminodiethylate hydrogen borate, butylaminodiethylate hydrogen borate, octadecylaminodiethylate hydrogen borate, dodecylaminodiethylate hydrogen borate, cyclohexylaminodiethylate hydrogen borate, phenylaminodiethylate hydrogen borate, oleylaminodiethylate hydrogen borate, cocoaminodiethylate hydrogen borate, and tallowaminodiethylate hydrogen borate and mixtures thereof.

It should be noted that a transition metal having an atomic number between 21 and 30 or a Group IVA metal of the Periodic Table may be incorporated into the boramid compounds herein. When a transition metal is incorporated into said compound, the metal compound will replace the hydrogen atom on the hydroxy portion of the structure. In addition, the Examples, as set forth hereinafter, recite cocoaminodiethylate hydrogen borate as boramid C/12, tallowaminodiethylate hydrogen borate as boramid T/12 and octadecylaminodiethylate hydrogen borate as boramid 18/12. The corresponging metalboron derivatives will, of course, incorporate the desired metal into the composition before the boramid nomenclature, for example, zinc boramid C/12, etc.

Metals are conveniently incorporated into the boramid compound using conventional methods and apparatus. Normally, the metal is reacted with the desired boramid compound in salt form. Thus the metal acetates, propanates, hexanates etc. are suitable for use. It should be noted that not all metal salts are desirable for incorporating the metal ion into the boramid compound. The metal carbonates, nitrates, oxalates, chlorides, sulfates, hydroxides and oxides, to name a few, are all undesirable as vehicles for imparting metal ions into the boramid compound. These metal salts experience solubility problems, separation problems and in addition, undesirable ions are frequency left in the boramid compound.

Desirable metals are conveniently selected from first row transition metals of the Periodic Table. Transition metals which are suitable for use are selected from scandium, titanium, vanadium, chromium, manganese, iron, cobalt, nickel, copper, zinc and mixtures thereof. Group IVA metals which are useful herein include tin and lead and mixtures thereof. Normally, the metal will comprise from about 1 to about 17 weight percent, preferably from about 5 to about 10 weight percent of the boramid compound.

Generally, when two different boramid compounds or derivatives thereof are blended together, a weight ratio of from about 1:20 to about 20:1, preferably from about 1:10 to about 10:1 is highly desirable for imparting extreme pressure, anti-wear and friction reducing properties to a lubricant.

The invention will be further described with reference to the following Examples.

EXAMPLE I

A boramid compound is prepared by adding 20 grams of boric acid, 95 grams of Armak Ethomeen C/12 [bis(2-hydroxyethyl) cocoamine] and 250 ml of toluene to a single-necked one liter round-bottomed flask. The toluene acts as a solvent and as an azeotrope for water produced during the reaction. It should be noted that boric acid is not soluble in toluene or Ethomeen C/12. The flask is placed in a heating mantle and fitted with a Dean-Stark trap that is topped with a condenser. The mixture thus formed is, then, heated until it begins to reflux. Next, the mantle is adjusted to give a moderate reflux rate. The reaction mixture is refluxed for one hour, or until the stoichiometric amount of water (12 ml.) collects in the Dean-Stark trap and all of the boric acid has dissolved, after which the toluene is distilled from the reaction product. The reaction product (103 grams) is designated boramid C/12 and has a clear golden color. Boramid C/12 is a fluid liquid while hot but sets into a soft viscous material when cooled to room temperature. The compound is readily soluble in hydrocarbon solvents and water.

EXAMPLE II

A boramid compound is prepared by following the procedure of Example I with the following substitution:

Armak Ethomeen T/12 [bis(2-hydroxyethyl) tallowamine] is substituted for the Armak Ethomeen C/12. Substantially the same results are obtained, however, the resulting compound is designated boramid T/12.

EXAMPLE III

A boramid compound is prepared by mixing 20 grams of boric acid, 95 grams of Armak Ethomeen 18/12 [bis(2-hydroxyethyl) octadecylamine] and, as a solvent, 250 ml of toluene in a single-necked on liter round-bottomed flask. The flask is placed in a heating mantle and fitted with a Dean-Stark trap and water cooled condenser. The mixture is heated under reflux for one hour, during which 12 ml of water collects in the Dean-Stark trap. The toluene is then distilled from the reaction product. The compound is designated boramid 18/12 and is readily soluble in hydrocarbon solvents and water.

EXAMPLE IV

The procedure of Example III is followed to prepare a boramid compound with the following exception: N,N-diethanol-n-methylamine (46.3 grams) is substituted for the Armak Ethomeen 18/12. The reaction product thus produced is a liquid product with the consistency of honey when hot and becomes a waxy semi-solid when cooled to room temperature.

EXAMPLE V

Boric acid (20 grams), N,N-diethanol-N-phenylamine (46.3 grams) and 250 mls of toluene are mixed in a one liter single-necked flask to prepare a boramid compound. The flask is equipped with a heating mantle, Dean-Stark trap and water-cooled condenser. The mixture is heated under reflux until the reaction is completed (12 ml of water collects), approximately one hour, and the toluene is distilled from the reaction mixture. The product thus prepared is suitable for use as an extreme pressure antiwear and friction reducing additive for lubrication compositions.

EXAMPLE VI

A metal derivative of boramid C/12 is prepared by mixing 54 grams of the product of Example I (boramid C/12), 400 ml of toluene, 24.6 grams of nickel acetate and 150 ml of methanol in a single-necked, one liter round bottom flask which is equipped with a heating mantle and water-cooled condenser. The mixture is refluxed for four hours. Next, water, toluene, methanol and acetic acid are distilled from the reaction product. The product (59 grams) contained 7.8 weight percent nickel as determined by emission spectroscopy and the resulting product is a fluid green liquid when hot, which turns into a solid upon cooling to room temperature. The product is readily soluble in hydrocarbon solvents and water.

EXAMPLE VII

A metal boramid is prepared by following the procedure of Example II with the following exception: the boramid T/12 (54 grams), 400 ml of toluene, 24 grams of nickel acetate and 150 mls of methanol are mixed in a single-necked, one liter round bottom flask, equipped with a heating mantle, Dean-Stark trap and water-cooled condenser. The mixture is refluxed for four hours and the toluene, water and acetic acid are distilled from the reaction product.

EXAMPLE VIII

A zinc derivative of boramid C/12 is prepared by mixing 54 grams of the reaction product of Example I (boramid C/12) with 400 ml toluene, 19.1 grams of zinc acetate and 50 ml of methanol in a single-necked, one liter round bottom flask, equipped with a heating mantle and water-cooled condenser. The mixture is refluxed for four hours and the toluene, methanol, water and acetic acid are distilled. The resulting product is suitable for use as an extreme pressure, anti-wear, friction reducing additive for lubricating composition.

EXMPLE IX

A metal boramid is prepared by following the procedure of EXAMPLE VII with the following exception: zinc acetate is substituted for the nickel acetate to produce zinc-boramid T/12.

It is to be noted that transition metals having an atomic number between 21 and 30, and Group IVA metals of the Periodic Table may be substituted for the nickel and zinc metals herein to prepare corresponding metal boramids.

EXAMPLE X

The extreme pressure, anti-wear and friction reducing additives, boramid C/12 and nickel-boramid C/12 produced in Examples I and VI in a 1:1 ratio mixture are mixed with 450 neutral oil and evaluated for performance. The additive mixture is mixed with the 450 neutral oil at 5 weight percent based on the total weight of the lubricant composition. The boramid C/12, nickel-boramid C/12 and 450 neutral oil mixture is compared to Arco graphite lubricant and ASTM high reference oil, SAE 20W/30 for friction reduction and extreme pressure properties.

the above lubricant is tested in accordance with the procedure disclosed in ASTM D3233-73 (Reapproved 1978) using a Falex lubricant tester. The test is performed by applying resistance to a revolving metal journal. Resistance is applied by two V-Blocks equipped with a ratchet mechanism which steadily increases pressure on the journal. The metal journal and V-Blocks are composed of steel in this example. The metal journal and V-Blocks are submerged in the lubricating composition to be tested. The results are indicated in Table 1 below.

TABLE 1

| | LUBRICANT | | | |
| | Torque on Journal (lbs-in.) | | | |
| True Load lbs | 450 Neutral Oil - No Additives | 450 Neutral Oil With Boramid C/12 and Ni—Boramid C/12 mixture (1:1 ratio) | Arco Graphite | ASTM SAE 20W/30 |
|---|---|---|---|---|
| 300 | 8 | 4 | 6 | 6 |
| 500 | 11 | 6 | 8 | 7 |
| 750 | 16 | 9 | 16 | 12 |
| 1000 | Journal Shear | 14 | 21 | 20 |
| 1250 | — | 21 | 26 | 24 |
| 1500 | — | Journal Shear | Journal Shear | Journal Shear |

It should be noted that substantially the same results are obtained when nickel-boramid T/12 additive is substituted for the nickel-boramid C/12 additive above.

EXAMPLE XI

A boramid C/12, nickel-boramid C/12 and neutral 450 oil mixture is tested in accordance with the procedure set forth in Example X with the following exception: the metal Journal and V-Blocks are constructed from cast iron. The results are indicated in Table 2 below.

TABLE 2

| | LUBRICANT | | |
| | Torque on Journal (lbs-in.) | | |
| True Load, lbs | 450 Neutral Oil- with Boramid C/12 and Ni—Boramid Mixture (1:1 ratio) | Arco Graphite | ASTM SAE 20W/30 |
|---|---|---|---|
| 300 | 3 | 6 | 6 |
| 500 | 4 | 7 | 7 |
| 750 | 7 | 13 | 10 |
| 1000 | 12 | 15 | 14 |
| 1250 | 14 | 17 | 17 |
| 1500 | 16 | 20 | 19 |
| 1750 | 18 | 23 | 21 |
| 2000 | Journal Wear | 24 | Journal Wear |
| 2250 | — | Journal Wear | — |

Nickel-boramid T/12 may conveniently be substituted for the nickel-boramid C/12 above with substantially the same results.

EXAMPLE XII

A boramid C/12, nickel-boramid, 450 neutral oil mixture is tested in accordance with the procedure set forth in Example X with the following exception: The Journal is constructed from cast iron and the V-Blocks are constructed from chrome. The lubricant properties of the boramid C/12, nickel-bormid C/12 and 450 neutral oil mixture are compared with those of Arco graphite and ASTM, SAE 20 W/30 lubricants. The lubricant compositions are tested in accordance with the procedure disclosed in ASTM:D3233-73 (Reapproved 1978) using a Falex Lubricant tester. The results are indicated in Table 3 below.

TABLE 3

| | Torque on Journal (lbs-in.) | | |
| | 450 Neutral Oil with Boramid C/12 Ni—Boramid C/12 | | |
| True Load, lbs | mixture (1:1 ratio) | Arco Graphite | ASTM SAE 20W/30 |
|---|---|---|---|
| 300 | 5 | 4 | 5 |
| 500 | 6 | 5 | 7 |
| 750 | 7 | 8 | 10 |
| 1000 | 12 | 11 | 14 |
| 1250 | 15 | 16 | 20 |
| 1500 | Journal Wear | Journal Wear | Journal Wear |

EXAMPLE XIII

An extreme pressure, anti-wear and friction-reducing lubricant composition is prepared by mixing 5 weight percent of the zinc-boramid C/12 additive of Example VIII with 450 neutral oil. The lubricant composition reduces wear and friction of metal components in moving contact with each other and, in addition, lubricates said metal surfaces under extreme pressure or boundary lubrication conditions.

EXAMPLE XIV

The zinc-boramid T/12 additive of Example IX is admixed with 450 neutral oil at 5 percent by weight based upon the total lubricant composition to prepare an extreme pressure, anti-wear and friction reducing lubricant composition. The zinc-boramid T/12 additive imparts extreme pressure, antiwear and friction reducing properties to the 450 neutral, lubricating oil.

EXAMPLE XV

A lubricant composition containing nickel-boramid C/12 and 450 neutral oil are tested for extreme pressure, anti-wear and friction reducing properties in a 1973 Chevrolet 350 cu. in. displacement V-8 engine which is run continuously for 196 hours on a single fill of the lubricating composition. The lubricating oil does not contain conventional zinc dialkydithiophosphate anti-wear additives. The lubricant composition is disclosed in detail in Table 4 below.

TABLE 4

| Compound | Weight Percent |
|---|---|
| 450 neutral oil | 89.965 |
| Boramid C/12 | 2.5.000 |
| Nickel-boramid C/12 | 2.5.000 |
| Oronite OLOA 1200[A] | 4.000 |
| Chlorowax 40[B] | 1.000 |
| UNAD 242[C] | 0.010 |
| Terphthalic Acid[D] | 0.005 |
| Quinizarin[E] | 0.020 |

[A]Oronite OLOA 1200 - alkyl succinimide type ashless dispersant.
[B]Chlorowax 40 - Chlorided paraffin containing 40% chlorine.
[C]UNAD 242 - Silicone type defoamant containing kerosene.
[D]Terphthalic acid - Corrosion inhibitor.
[E]Quinizarin - Antioxidant.

The Chevrolet engine is programmed to run in a repeating cycle that averaged approximately 40 MPH. The cycle is disclosed in Table 5 below.

TABLE 5

| Cycle | RPM | Speed(MPH) | Time(MIN.) |
|---|---|---|---|
| 1 | 700 | 0 | 2.0 |
| 2 | 1700 | 45 | 3.0 |
| 3 | 1200 | 30 | 4.0 |
| 4 | 2225 | 60 | 7/60 |

TABLE 5-continued

| Cycle | RPM | Speed(MPH) | Time(MIN.) |
|---|---|---|---|
| 5 | 2400 | 65 | 3.0 |

After the 196 hour engine test is completed, several areas in the engine which are subject to wear are closely examined. These areas include: main bearings, top end bearings, cam shaft bearings, valve lifters and cham shaft lobes.

The length of the engine run is equivalent to approximately 8,000 miles of driving. A detailed examination of the above-described components indicated no abnormal or excessive wear.

EXAMPLE XVI

The extreme pressure, anti-wear and friction reducing additives boramid C/12 produced in Example I and boramid T/12 produced in Example II are sequentially mixed with SAE 10 W/40 motor oil[a] containing 0.15 weight percent of phosphorous and 0.17 weight percent of zinc. In addition, the motor oil contains 0.21 weight percent of calcium.

[a]Union Super Motor Oil, marketed commercially by the Union Oil Company of California.

The additive and/or lubricant composition is tested in accordance with the procedure disclosed in ASTM D3233-73 (Reapproved 1978) using a Falex lubricant tester. The test, in accordance with the above ASTM designation, is performed by applying resistance to a revolving metal journal. A ratchet mechanism movably attached to two V-Blocks applies resistance by steadily increasing pressure on the journal. The metal journal and V-Blocks (steel) are submerged in the lubricant composition to be tested.

TABLE 6

| | Torque on Journal (lbs.-in.) | | |
|---|---|---|---|
| True Load lbs | SAE 10W/40[a] Without Additive | SAE 10W/40 With 1% Boramid C-12 | SAE 10W/40 With 1% Boramid T-12 |
| 100 | 8 | 7½ | 7½ |
| 250 | 12 | 10 | 9 |
| 500 | 19 | 15 | 14 |
| 750 | 22 | 18 | 19 |
| 1,000 | 25 | 22 | 22 |
| 1,250 | 35 | 25 | 25 |
| 1,500 | Journal Shear | 27 | 27 |
| 1,750 | — | Journal Shear | 33 |
| 2,250 | — | — | Journal Shear |

[a]Union Super Motor Oil, marketed commercially by the Union Oil Company of California.

EXAMPLE XVII

A metal-boramid is prepared by following the procedure of Example VI with the following changes: 31 grams of boramid C/12 is mixed with 19 grams of lead (II) acetate, 150 ml. of toluene and 25 ml of methanol. The mixture is refluxed for 2 hours, after which, the toluene, methanol, water and acetic acid (produced from acetate) are distilled using conventional techniques and apparatus. The resulting lead-boramid C/12 product (32.6 grams) is a golden colored oil with the consistency of honey.

EXAMPLE XVIII

The extreme pressure, anti-wear and friction reducing additive, lead-boramid C/12 produced in accordance with the procedure of Example XVII is blended with 450 neutral oil at 5 percent by weight based on the total weight of the lubricant composition. The above, lubricant composition is compared to Arco graphite lubricant and ASTM high reference oil, SAE 20W-30 for friction reduction and extreme pressure properties:

The lead-boramid C/12 and 450 neutral oil mixture is compared to Arco graphite and ASTM, SAW 20E-30 in accordance with the procedure disclosed in ASTM:D3233-73 (Reapproved 1978) using a Falex Lubricant tester. The test is performed by applying resistance to a revolving metal journal. Resistance is applied by two V-Blocks equipped with a ratchet mechanism which steadily increases pressure on the journal. The metal journal and V-Blocks are composed of steel in this example. The metal journal and V-Blocks are submerged in the lubricating composition to be tested. The results are indicated in Table 7 below.

TABLE 7

| | Torque on Journal (lbs.-in.) | | |
|---|---|---|---|
| True Load (lbs) | 450 Neutral Oil with Lead-Boramid C/12 | Arco Graphite | ASTM SAE 20W-30 |
| 300 | 7 | 6 | 6 |
| 500 | 11 | 8 | 7 |
| 750 | 14 | 16 | 12 |
| 1000 | 20 | 21 | 20 |
| 1250 | 23 | 26 | 24 |
| 1500 | 40 | Journal Shear | Journal Shear |
| 1750 | 85 | | |
| 2000 | 94 | | |
| 2250 | 90 | | |
| 2500 | 71 | | |
| 2750 | 79 | | |
| 3000 | 70 | | |
| 3250 | 70 | | |

Stopped due to inability to increase load.

EXAMPLE XIX

A copper-boramid is prepared by adding 62 grams of boramid C/12, 150 ml of toluene, 50 ml of water and 18.2 grams of cupric acetate to a 500 ml., single necked round bottom flask equipped with a Dean-Stark trap and condenser. The mixture is refluxed for 8 hours, after which, water, toluene and produced acetic acid (from acetate) are distilled leaving 68 grams of a green solid.

EXAMPLE XX

The copper-boramid C/12 additive produced in Example XIX is admixed with 450 neutral oil at 5 weight percent based on the total weight of the lubricant composition and evaluated for performance in accordance with the procedure of Example XVIII with the following exception: the lubricant properties of the copper-boramid, 450 neutral oil mixture are compared with those of 450 neutral oil and SAE 10W-40 lubricants. The results are indicated in Table 8 below:

TABLE 8

| | Torque on Journal (lbs.-in.) | | |
|---|---|---|---|
| True Load (lbs) | 450 Neutral Oil with Copper-Boramid C/12 | 430 Neutral Oil Without Additive | ASTM 10W-40 |
| 300 | 9 | 10 | — |
| 500 | 11 | 15 | 17 |
| 750 | 17 | 23 | 21 |
| 1000 | 20 | Journal Shear | 28 |
| 1250 | 28 | | 33 |
| 1500 | 55 | | Journal |

TABLE 8-continued

| True Load (lbs) | Torque on Journal (lbs.-in.) | | |
|---|---|---|---|
| | 450 Neutral Oil with Copper-Boramid C/12 | 430 Neutral Oil Without Additive | ASTM 10W-40 |
| | | | Shear |
| 1750 | 55 | | |
| 2000 | 55 | | |
| 2250 | 60 | | |
| 2500 | 70 | | |
| 2750 | 75 | | |
| 3000 | 80 | (Stopped for inspection). | |

As can readily be determined from the above Examples, the additives herein impart extreme pressure, anti-wear and friction reducing properties to lubrication compositions when used in accordance with the disclosure herein. Obviously, many modifications and variations of the invention, as hereinbefore set forth, may be made without departing from the spirit and scope thereof, and therefore only such limitations should be imposed as are indicated in the appended claims.

We claim:

1. An extreme pressure, anti-wear lubricating composition comprising a major amount of a lubricating oil and a minor amount of an extreme pressure, anti-wear additive of the formula:

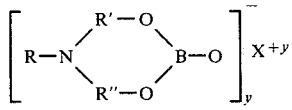

wherein R is hydrogen, alkyl, cyclic, alicyclic, aryl, alkylaryl or arylalkyl radical having from about 1 to about 24 carbon atoms, R' and R" are either straight or branched carbon chain, cyclic or alicyclic radicals having from 2 to about 20 carbon atoms, y is an integer from 1 to 4, and X is either hydrogen or a metal selected from a transition metal having an atomic number between 21 and 30 or a Group IVA metal and mixtures thereof.

2. The extreme pressure, anti-wear lubricating composition of claim 1, wherein the additive comprises from about 0.1 to about 15 percent by weight of the composition.

3. The extreme pressure, anti-wear lubrication composition of claim 1, wherein R is hydrogen, alkyl, cyclic, alicyclic, aryl, alkylaryl or arylalkyl having from about 1 to about 18 carbon atoms.

4. The extreme pressure, anti-wear lubricating composition of claim 1, wherein R' and R" are straight or branched carbon chains, cyclic alicyclic radicals having from about 2 to about 10 carbon atoms.

5. The extreme pressure, anti-wear lubricating composition of claim 1, wherein the additive is selected from the group consisting of methylaminodiethylate hydrogen borate, ethylaminodiethylate hydrogen borate, propylaminodiethylate hydrogen borate, butylaminodiethylate hydrogen borate, octadecylaminodiethylate hydrogen borate, dodecylaminodiethylate hydrogen borate, cyclohexylaminodiethylate hydrogen borate, phenylaminodiethylate hydrogen borate, oleylaminodiethylate hydrogen borate, cocoaminodiethylate hydrogen borate and tallowaminodiethylate hydrogen borate and mixtures thereof.

6. The extreme pressure, anti-wear lubricating composition of claim 1, wherein the additive comprises from about 0.5 to about 10 weight percent of boron.

7. The extreme pressure, anti-wear lubricating composition of claim 1, wherein the lubrication oil is selected from mineral oil, crude oil, grease, distillate fuel oil, synthetic oil and cutting oil, and mixtures thereof.

8. The extreme pressure, anti-wear lubricating composition defined in claim 1 where R is alkyl having from 1 to about 24 carbon atoms.

9. An extreme pressure, anti-wear lubricating composition comprising a major amount of a lubricating oil and a minor amount of an extreme pressure, anti-wear additive selected from, ethylaminodiethylate hydrogen borate, propylaminodiethylate hydrogen borate, butylaminodiethylate hydrogen borate, octadecylaminodiethylate hydrogen borate, dodecylaminodiethylate hydrogen borate, cyclohexylaminodiethylate hydrogen borate, phenylaminodiethylate hydrogen borate, oleylaminodiethylate hydrogen borate, cocoaminodiethylate hydrogen borate, or tallowaminodiethylate hydrogen borate and mixtures thereof.

10. An extreme pressure, anti-wear lubricating composition comprising a lubricating oil and from about 0.1 to about 15 weight percent of an extreme pressure, anti-wear additive selected from methylaminodiethylate hydrogen borate, phenylaminodiethylate hydrogen borate, octadecylaminodiethylate hydrogen borate, cocoaminodiethylate hydrogen borate and tallowaminodiethylate hydrogen borate and mixtures thereof.

11. An extreme pressure, anti-wear lubricating composition comprising a major amount of a lubricating oil and a minor amount of an extreme pressure, anti-wear additive of the formula:

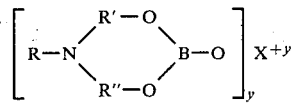

wherein R is hydrogen, alkyl, cyclic, alicyclic, aryl, alkylary or arylalkyl radical having from about 1 to about 10 carbon atoms, R' and R" are either straight or branched carbon chains having from 2 to about 20 carbon atoms, y is an integer of 1 to 4, and X is either hydrogen or a metal selected from a transition metal having an atomic number between 21 and 30 or a Group IV metal and mixtures thereof.

12. The extreme pressure, anti-wear lubricating composition of claim 11, wherein the additive is selected from the group consisting of methylaminodiethylate hydrogen borate, ethylaminodiethylate hydrogen borate, propylaminodiethylate hydrogen borate, butylaminodiethylate hydrogen borate, octadecylaminodiethylate hydrogen borate, dodecylaminodiethylate hydrogen borate, phenylaminodiethylate hydrogen borate, oleylaminodiethylate hydrogen borate, cocoaminodiethylate hydrogen borate and tallowaminodiethylate hydrogen borate and mixtures thereof.

13. The extreme pressure, anti-wear lubricating composition defined in claim 11 where R is alkyl having from 1 to about 24 carbon atoms.

14. An extreme pressure, anti-wear lubricating composition comprising a major amount of a lubricating oil and a minor amount of an extreme pressure, anti-wear additive of the formula:

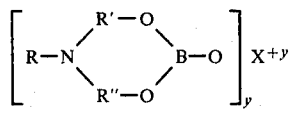

wherein R is hydrogen alkyl, cyclic, alicyclic, aryl, alkylaryl or arylalkyl radical having from about 1 to about 24 carbon atoms, R' and R" are straight or branched alkyl carbon chains having from 2 to about 10 carbon atoms, y is an integer of 1 to 4, and X is either hydrogen or a metal selected from a transition metal having an atomic number between 21 and 30 or a Group IV metal and mixtures thereof.

15. The extreme pressure, anti-wear lubricating composition of claim 14, wherein the additive is selected from the group consisting of methylaminodiethylate hydrogen borate, ethylaminodiethylate hydrogen borate, propylaminodiethylate hydrogen borate, butylaminodiethylate hydrogen borate, octadecylaminodiethylate hydrogen borate, dodecylaminodiethylate hydrogen borate, cyclohexylaminodiethylate hydrogen borate, oleylaminodiethylate hydrogen borate, cocoaminodiethylate hydrogen borate and tallowaminodiethylate hydrogen borate and mixtures thereof.

16. The extreme pressure, anti-wear lubricating composition defined in claim 14 where R is alkyl having from 1 to about 24 carbon atoms.

* * * * *

UNITED STATES PATENT OFFICE
CERTIFICATE OF CORRECTION

Patent No. 4,400,284　　　　　　　　　Dated　August 23, 1983

Inventor(s)　Peter Jessup et al.

It is certified that error appears in the above-identified patent and that said Letters Patent are hereby corrected as shown below:

Column 16, line 46 (claim 11) "about 10 carbon atoms" should read -- about 18 carbon atoms --.

Signed and Sealed this

Seventh Day of August 1984

[SEAL]

Attest:

Attesting Officer

GERALD J. MOSSINGHOFF

Commissioner of Patents and Trademarks